United States Patent [19]

Runkel et al.

[11] Patent Number: 5,035,891
[45] Date of Patent: Jul. 30, 1991

[54] CONTROLLED RELEASE SUBCUTANEOUS IMPLANT

[75] Inventors: Richard A. Runkel, Palo Alto; Jung-Chung Lee, San Jose, both of Calif.

[73] Assignee: Syntex (U.S.A.) Inc., Palo Alto, Calif.

[21] Appl. No.: 398,106

[22] Filed: Aug. 24, 1989

Related U.S. Application Data

[63] Continuation of Ser. No. 105,149, Oct. 5, 1987, abandoned.

[51] Int. Cl.$^5$ .............................................. A61F 13/00
[52] U.S. Cl. ................................... 424/423; 424/422; 424/438; 424/473
[58] Field of Search ................ 424/473, 422, 423, 438

[56] References Cited

U.S. PATENT DOCUMENTS

| 3,939,265 | 2/1976 | Grandadam | 514/170 |
|---|---|---|---|
| 3,948,254 | 4/1976 | Zaffaroni | 424/423 |
| 3,992,518 | 11/1976 | Chien | 424/425 |
| 4,180,560 | 12/1979 | Katz | 424/426 |
| 4,207,890 | 6/1980 | Mamajer et al. | 424/473 |
| 4,210,644 | 7/1980 | Ewing | 514/170 |
| 4,220,153 | 9/1980 | Presback | 424/473 |
| 4,315,925 | 2/1982 | Hussain | 514/177 |
| 4,326,525 | 4/1982 | Swanson | 424/473 X |
| 4,331,651 | 5/1982 | Reul et al. | 424/434 |
| 4,333,919 | 6/1982 | Kleber et al. | 424/438 |
| 4,404,183 | 9/1983 | Kawata | 424/499 |
| 4,432,964 | 2/1984 | Shell | 424/427 |
| 4,524,060 | 6/1985 | Mughal | 424/459 |
| 4,666,702 | 5/1987 | Junginger | 424/473 X |
| 4,765,980 | 8/1988 | DePrince | 424/423 X |
| 4,786,501 | 11/1988 | Janski et al. | 424/422 |
| 4,816,568 | 3/1989 | Hamilton, Jr. et al. | 530/399 |
| 4,927,633 | 5/1990 | Eckenhoff et al. | 424/438 |

FOREIGN PATENT DOCUMENTS

| 9044310A | 9/1982 | Japan . |
| 2010676 | 7/1979 | United Kingdom . |
| 2136688A | 9/1984 | United Kingdom . |
| 2154138A | 9/1985 | United Kingdom . |
| 2167662A | 6/1986 | United Kingdom . |

OTHER PUBLICATIONS

"Inhition and Control of Estrus and Ovulation in Ewes with a Subcutaneous Implant of Silicone Rubber Impregnated with a Progestogen" by P. J. Dziuk et al., *Am. J. Vet. Res.*, 29, 2413–2417 (1968).
"Controlled Release of Testosterone Using Silicone Rubber" by R. Shippy et al., *J. Biomed. Mater. Res.*, 7, 95–110 (1973).
"Release of Progesterone from Silicone Rubber Implants in Vitro, and the Effects of the Implants on Plasma Progesterone Levels in Sheep" by N. Cunningham et al., *J. Reprod. Fert.*, 43, 555–558 (1975).
"Release Rate of Testosterone and Estrogens from Polydimethylsiloxane Implants for Extended Periods in Vivo Compared with Loss in Vitro" by W. Greene et al., *Int. J. Fertil.*, 23, 128–132 (1978).
H. Nash et al., "Steroid Release from Silastic Capsules and Rods" *Contraception* 18, 367–394 (1978) ("Nash").
"Maintenance of Physiologic Concentrations of Plasma Testosterone in the Castrated Male Dog, Using Testosterone-Filled Polydimethylsiloxane Capsules" by D. Vincent et al., *Am. J. Vet. Res.*, 40, 705–706 (1979).
"The Absorption, Distribution and Excretion of Anabolic Agents" by R. Heitzman, *J. Animal Sci.*, 57, 233–238 (1983).
"Plasma Testosterone Level in Adult Neonatal Female Rats Bearing Testosterone Proprionate-Filled Silicone Elastomer Capsules for Varying Periods of Time", by E. Sommerville et al., *J. Endocr.*, 98, 365–371, (1983).
"Effect of Monensin, Estradiol Controlled Release Implants and Supplement on Performance in Grazing Steers", by J. Wagner et al., *J. Animal Sci*, 58, 1062–67 (1984).
"Controlled-Release Delivery Systems for Hormones" by L. Beck et al., *Drugs*, 27, 528–547 (1984).
"Enhanced Release of Drugs from Silicone Elastomers: (IV) Subcutaneous Controlled Release of Indomethacin and In Vivo/In Vitro Correlations" by D. Hsieth et al., *Drug Devel. and Indust. Pharm.*, 11, 1447–1466 (1985).
"Enhanced Release of Drugs from Silicone Elastomers (I) Release Kinetics of Pineal and Steroidal Hormones" by D. Hsieth et al., *Drug. Devel and Insdust. Pharm.*, 11, 1391–1410 (1985).
"Release Rate of MGA from Polyurethane Polymers", by M. Ogilvie et al., *J. Animal Sci.*, 35, 251 (Abstract).
"Induction of Male Sex Behavior in Ewes Using Silastic Implants Containing Testosterone Proprionate", by N. Scheffrahn et al., *J. Animal Sci.*, 51, 108–109 (Abstract).

Primary Examiner—Thurman Page
Assistant Examiner—Louis A. Piccone
Attorney, Agent, or Firm—Carol J. Roth; Derek P. Freyberg; Tom M. Moran

[57] ABSTRACT

A sustained release, reservoir-type subcutaneous implant device for the sustained administration to a subject of a biologically active compound comprises:
an effective amount of a biologically active compound;
an amount of a solid hydrophilic polymer sufficient to cause swelling of the device by osmotic pressure after implantation;
an effective amount of a solubilizing agent; and
a sufficient amount of a non-porous rate-controlling membrane which completely encapsulates said biologically active compound, wherein said rate-controlling membrane is permeable to said biologically active compound, but is impermeable to said solubilizing agent. This device is particularly advantageous for the administration of growth promoting compounds to livestock.

29 Claims, No Drawings

CONTROLLED RELEASE SUBCUTANEOUS IMPLANT

This is a continuation of pending application Ser. No. 07/105,149, filed Oct. 5, 1987 now abandonded, incorporated herein by reference.

BACKGROUND OF THE INVENTION

1. Field of the Invention

This invention relates to a novel implant capable of releasing a therapeutic agent at a constant rate over a prolonged period of time, and a method for treating a mammalian or avian subject using said implant.

2. Related Disclosure

The advantages of employing sustained-release drug implants are well known in the art. Many therapeutic agents are rapidly metabolized or are cleared from the subject's system, necessitating frequent administration of the drug to maintain a therapeutic concentration. There exists a need for a sustained release device capable of administering an active compound at a relatively constant rate, where the rate is high enough to effect and maintain an effective concentration. Preferably, such a device would be inexpensive and easily manufactured.

Steroids are frequently administered to livestock to increase feed efficiency. For example, steroids such as progestogen derivatives are frequently administered to beef cattle to increase the quality of the meat produced, and increase the yield of meat per amount of feed consumed. Progestongens are more effective when coadministered with an estrogen derivative. For example, Synovex® S implants, which are administered to steers, are cylindrical pellets containing a mixture of estradiol benzoate and progesterone. Estrogen may not be administered orally, necessitating a parenteral form of delivery.

There is a variety of means by which the art has attempted to prepare suitable sustained release devices. Such devices may be designed typically for oral, rectal, or subcutaneous administration. The mode of administration is usually critical to the design of a sustained release device, due to the difference of biological environment. For example, a device for subcutaneous implantation must be non-irritating, and must be mechanically strong enough to withstand flexion or impact. A device for oral administration must be designed for resistance to gastric acidity and sensitivity to pH change.

Some devices are "matrix" type, and consist of an active compound dispersed in a matrix of carrier material. The carrier material may be either porous or non-porous, solid or semi-solid, and permeable or impermeable to the active compound. Matrix devices may be biodegradable, i.e., they may slowly erode after administration. Alternatively, matrix devices may be nondegradable, and rely on diffusion of the active compound through the walls or pores of the matrix. Matrix devices may be easily prepared, but are not suitable for administering some compounds. It is extremely difficult to prepare matrix devices that release active compound at a constant rate (i.e., zero order kinetics), as the release rate is typically a function of the active compound's concentration in the matrix. We are unaware of any published example of zero order release from a matrix device. As the amount of active compound remaining declines, the rate of release diminishes.

Other devices are "reservoir" type, and consist of a central reservoir of active compound surrounded by a rate controlling membrane (rcm). The rcm may be either porous or non-porous, but is not usually biodegradable. It is typically easier to prepare a reservoir device capable of zero order kinetics (independent of active compound concentration), as the release rate often depends only on the surface area of the rcm. However, reservoir devices often suffer from an inadequate rate of delivery: the rcm surface area required to maintain an effective concentration of active compound is frequently so large that it is impractical to administer the device. Additionally, reservoir devices are sensitive to rupture: if the rcm is breached, an excessive (possibly lethal) dose of active compound may be released instantaneously.

Some sustained release devices are hybrids, having a matrix core surrounded by a rcm. Other sustained release devices may be mechanical in nature, and include small compound-filled electrical or osmotic pumps. While these devices may be capable of zero order release, they are typically too expensive to compete economically with matrix and reservoir devices.

A number of implant devices are known in the art. UK Patent Application 2,010,676 to Wong, et al. discloses a reservoir device in the form of a flat, heat-sealed packet, cylindrical tube or "T" vaginal insert, comprising a rate controlling membrane, specifically ethylene-vinyl acetate copolymer or butylene terephthalate/polytetramethylene ether terephthalate. The active compound is presented in a carrier which is water-imbibing (to maintain, but not increase the size of the implant), and viscous to improve drug distribution within the device. These implants are useful for administering progesterone, estradiol, or d-norgestrel.

H. Nash, et al., "Steroid Release From Silastic Capsules and Rods" *Contraception*, 18, 367–394 (1978) discloses both reservoir and matrix implants fashioned from Silastic® polydimethylsiloxane, for sustained administration of contraceptive steroids. Nash's reservoir devices comprise Silastic® tubes (1.57 mm I.D., 2.41 mm O.D., and 2 or 3 cm in length) filled with steroid crystals. The matrix devices were prepared by mixing Silastic® monomer and steroid (25% by weight) with the catalyst, and pressing into molds to form rods 2.4 mm×2 or 3 cm. The steroids used were levonorgestrel, norethindrone, norethindrone acetate, testosterone, testosterone propionate, megestrol acetate, norgestrienone, norethandrolone, 17$\beta$-hydroxy-17$\alpha$-ethynyl-18-methyl-4,9,11-estriene-3-one, 17$\alpha$-ethyl-17-hydroxy-4-norandrosten-3-one, 16-methylene-17$\alpha$-acetoxy-19-norpregn-4-en-3,20-dione, and 17$\alpha$,21-dimethyl-19-norpregna-4,9-dien-3,20-dione. None of the implants released steroid with zero order kinetics. The average release rate in vivo ranged from 3.5 $\mu$g/cm/day (levonorgestrel for 367 days in humans) to 82.7±65 $\mu$g/cm/day (norethandrolone for 14 days in rats: the average rate after 112 days declined to 48.4 $\mu$g/cm/day).

D. Vincent, et al., "Maintenance of Physiologic Concentrations of Plasma Testosterone in the Castrated Male Dog, Using Testosterone-Filled Polydimethylsiloxane Capsules" *Am. J. Vet. Res.*, 40, 705–706 (1979) discloses a reservoir device comprising a Siloxane® tube (4.65 mm×7.5 cm) filled with crystalline testosterone, and implanted in castrated dogs.

R. Shippy, et al., "Controlled Release of Testosterone Using Silicone Rubber" *J. Biomed. Mater. Res.*, 7, 95–110 (1973) discloses a reservoir device comprising a crystalline testosterone cylinder dipped in Silastic ® or a Silastic ®/testosterone suspension.

N. Cunningham, et al., "Release of Progesterone from Silicone Rubber Implants In Vitro, and the Effects of the Implants on Plasma Progesterone Levels in Sheep" *J. Reprod. Fert.*, 43, 555–558 (1975), discloses a reservoir device comprising Silastic ® tubing packed with solid progesterone, incubated in 0.9% aqueous NaCl. One implant contained progesterone dissolved in arachis oil, which resulted in a lower rate of release than the implants containing solid progesterone. The implants prepared ranged from 6 to 10 cm in length, and from 1.97 to 6.36 mm in diameter, containing from 22.5 mg to 300 mg of progesterone, but were unable to maintain an effective concentration progesterone in ewes. Cunningham also discloses solid Silastic ® matrix implants containing progesterone, which achieved results superior to the reservoir devices. Matrix rods 10 cm×0.5 cm containing 205 to 293 mg of progesterone were capable of administering effective levels.

Additional reservoir devices are disclosed in L. Beck, et al., "Controlled-Release Delivery Systems for Hormones" *Drugs*, 27, 528–547 (1984): W. Greene et al., "Release Rate Of Testosterone and Estrogens from Polydimethylsiloxane Implants for Extended Periods In Vivo Compared with Loss In Vitro" *Int. J. Fertil.*, 23, 128–132 (1978): E. Sommerville, et al., "Plasma Testosterone Level In Adult and Neonatal Female Rats Bearing Testosterone Propionate-Filled Silicone Elastomer Capsules for Varying Periods of Time" *J. Endocr.*, 98, 365–371, (1983): U.S. Pat. Nos. 4,210,644: and 4,432,964.

U.S. Pat. No. 4,331,651 to Reul discloses a matrix device consisting of a silicone rubber depot for nasal administration to cattle. The rubber contains a "release promoting agent" which is liposoluble, scarcely soluble in water, and which may be an alcohol, ester, ether or ketone of 8–60 carbons. The "release promoting agent" should not "exude." The active compound is a steroid, optionally an antibiotic. Preferred steroids are testosterone and trenbolone acetate, optionally in combination with estrogens such as 17β-estradiol, and derivatives. The active compound may be dispersed in the rubber, or may be in tablet form (optionally containing PEGs etc.) wrapped in rubber. A preferred embodiment comprises only one tablet which is partially wrapped.

Japanese application J5 9044-310A to Nippon Kayaku discloses a matrix device consisting of a silicone rubber formulation containing a crystalline powdered dissolution assistant (especially a monobasic amino acid, e.g., glycine or alanine, NaCl or mannitol) and an antibiotic or anticancer drug. These devices achieve a release time of one week to one month.

UK Patent Application 2,167,662A to Dick discloses a matrix implant device in the form of a solid cylinder. The matrix is formed from a hydrophobic polymer, and delivers 17β-estradiol, testosterone, progesterone, nandrolone, trenbolone, or their acetates, propionates, benzoates, or zeranol, or combinations thereof. Dick discloses, as matrix materials, insoluble polypropylene, polyethylene, polyvinyl chloride, ethylvinyl acetate, polystyrene and polymethacrylate, as well as glycerol esters of the glycerol palmitostearate, glycerol stearate and glycerol behenate type.

D. Hsieh, et al., "Enhanced Release of Drugs From Silicone Elastomers: (IV) Subcutaneous Controlled Release of Indomethacin and In Vivo/In Vitro Correlations" *Drug Devel. and Indust. Pharm.*, 11, 1447–1466 (1985) discloses a matrix implant device comprising powdered indomethacin in a Silastic ® matrix, with varying concentrations of glycerol. Addition of glycerol caused the implant to swell, and increased the release rate. D. Hsieh, et al., "Enhanced Release of Drugs From Silicone Elastomers (I) Release Kinetics of Pineal and Steroidal Hormones" *Drug Devel. and Indust. Pharm.*, 11, 1391–1410 (1985) discloses a Silastic ® matrix device containing estradiol, 0–30% glycerol, and 0 or 10% NaCl, in an aqueous cosolvent system containing 0 or 10% PEG 400, propylene glycol, or glycerol. Hsieh found that the addition of glycerol, NaCl, and cosolvents increased the flux obtained from the matrix implant in in vitro experiments.

Matrix devices are also disclosed in P. J. Dziuk, et al., *Am. J. Vet. Res.*, 29, 2413–2417 (1968) "Inhibition and Control of Estrus and Ovulation in Ewes with a Subcutaneous Implant of Silicone Rubber Impregnated with a Progestogen": L. Beck, et al., *Drugs*, 27, 528–547 (1984) "Controlled-Release Delivery Systems for Hormones": R. Heitzman, *J. Animal Sci.*, 57, 233–238 (1983) "The Absorption, Distribution and Excretion of Anabolic Agents": J. Wagner, et al., *J. Animal Sci.*, 58, 1062–67 (1984) "Effect of Monensin, Estradiol Controlled Release Implants and Supplement on Performance in Grazing Steers": N. Scheffrahn, et al., *J. Animal Sci.*, 51, 108–109, "Induction of Male Sex Behavior In Ewes Using Silastic Implants Containing Testosterone Propionate": and N. Cunningham, et al., *J. Reprod. Fert.*, 43, 555–558 (1975), "Release of Progesterone from Silicone Rubber Implants In Vitro, and the Effects of the Implants on Plasma Progesterone Levels in Sheep".

U.S. Pat. No. 3,948,254 to Zaffaroni discloses a hybrid device comprising a solid matrix drug reservoir encapsulated in a microporous membrane, where the membrane pores are filled with a carrier material. The drugs disclosed include hormonal agents such as prednisolone, cortisone, cortisol and triamcinolone; androgenic steroids, such as methyltestosterone, fluoximesterone and the like; estrogenic steroids such as 17β-estradiol and ethinyl estradiol; progestational steroids, for example 17α-hydroxyprogesterone acetate, 19-norprogesterone, norethindrone, and the like.

UK Patent Application 2,154,138A to Roche discloses a hybrid subcutaneous implant for livestock weight promotion, using silicone rubber (Silastic, especially dimethylpolysiloxane) with estradiol dispersed in the rubber. The device is formed as a substantially hollow cylinder of the silicone rubber, with a core consisting of active ingredients (which may be steroids) dispersed in a biocompatible, biosoluble polymer which dissolves within days of implantation. The biocompatible, biosoluble polymer is a mixture of high molecular weight polyethylene glycol (PEG) and low molecular weight PEG, for example, PEG 3,000–10,000 with PEG 200–600. Thus, estradiol is released as if from a matrix (the silicone rubber wall), while the second active compound is released from a reservoir.

UK Application 2,136,688A to Ferguson discloses a delivery device of the type described in Roche above, but with an external dusting of antibiotic to improve retention.

U.S. Pat. No. 3,992,518 to Chien discloses another hybrid device comprising a membrane-wrapped silicone rubber matrix. The rubber matrix is prepared by forming an emulsion of rubber monomer and active compound in aqueous solution with a hydrophilic cosolvent, then crosslinking the monomer to form "microsealed compartments" containing the active compound in solution. The resulting matrix is then coated with a rate-controlling membrane. The rate-controlling membrane may be silicone rubber, ethylene/vinyl acetate, polyethylene terephthalate, butyl rubber, etc. The active compound is in a solution of water and a hydrophilic cosolvent not soluble in the rubber matrix. The hydrophilic cosolvent may be polyethylene glycol, propylene glycol, butylene glycol, etc., with PEG 400 preferred at a concentration of 20–70%. The hydrophilic cosolvent may also be an ionic or neutral surface active agent in aqueous concentration above the critical micelle concentration, preferably sodium dodecyl sulfate, polysorbates, cetyl trimethylammonium bromide, or cetylpyridinium chloride. Active compounds disclosed include ethynodiol diacetate, ethylnyl estradiol, estrone, estradiol, other estrogens, progesterone, and testosterone.

We have now found that one may prepare a particularly advantageous subcutaneous implant form by formulating compressed pellets containing a biologically active compound, a solubilizing agent, a solid, hydrophilic, non-toxic polymer sufficient to cause swelling by osmotic pressure after implantation, followed by wrapping the pellet(s) in a rate-controlling membrane which is permeable to the biologically active compound but is impermeable to the solubilizing agent. The implants so obtained are particularly advantageous in a number of respects:

- a long, zero-order release of greater than 90% of encapsulated biologically active compound is effected (zero-order release for greater than 230 days is attainable with the preferred embodiments);
- the length of the release period is a linear function of the amount of biologically active compound encapsulated, e.g., adding 20% more biologically active compound to an implant will result in a release period extended by 20% with no change in the rate of release per day;
- the biologically active compound is essentially completely administered (i.e., little or no undelivered residue remains within the device);
- use of the solubilizing agent increases the flux of biologically active compound through the rate-controlling membrane, thus allowing one to achieve a suitable flux with less membrane surface area (which in turn allows fabrication of a smaller device);
- the implant is small and easily administered—due to its small dimensions, it may be implanted using a hollow needle (cf. Norplant ® a five-year human contraceptive implant containing progestin, which requires six "matchstick-sized" capsules, and which results in overdosing during the first year in order to maintain sufficient levels for contraception during the following years);
- because the solubilizing agent is trapped inside the membrane, only a small amount is required, and the agent need not be non-irritating;
- the complete device is easily and inexpensively manufactured; and
- treatment may easily be terminated by removing the implant device.

SUMMARY OF THE INVENTION

One aspect of the invention is a reservoir-type device for the sustained administration of a biologically active compound, suitable for subcutaneous implantation, which device comprises an effective amount of a biologically active compound; an amount of a solid, hydrophilic, non-toxic polymer sufficient to cause swelling by osmotic pressure after implantation; an effective amount of a solubilizing agent; and a sufficient amount of a non-porous, rate-controlling membrane which completely encapsulates said biologically active compound, wherein said rate-controlling membrane is permeable to said biologically active compound, but is not permeable to said solubilizing agent or said solid hydrophilic polymer.

Another aspect of the invention is the method of treating a subject, which method comprises implanting subcutaneously an implant device of the invention.

DETAILED DESCRIPTION AND PREFERRED EMBODIMENTS

One aspect of the invention is a reservoir device for the sustained administration of a biologically active compound, suitable for subcutaneous implantation, which device comprises an effective amount of a biologically active compound; an amount of a solid, hydrophilic, non-toxic polymer sufficient to cause swelling by osmotic pressure after implantation; an effective amount of a solubilizing agent; and a sufficient amount of a non-porous, rate-controlling membrane which completely encapsulates said biologically active compound, wherein said rate-controlling membrane is permeable to said biologically active compound, but is not permeable to said solubilizing agent or said solid hydrophilic polymer. A preferred subgenus is the device wherein said biologically active compound is in the form of a pellet or a plurality of pellets, especially three to fifteen pellets. A preferred class of the invention is the device wherein said biologically active compound comprises a steroid or steroid derivative, particularly where said biologically active compound comprises an estrogen derivative in combination with a progestogen or an androgenic agent. A preferred subclass of the invention is the device wherein said estrogen derivative is estradiol benzoate, particularly where the estradiol benzoate is in combination with progesterone, testosterone propionate, or trenbolone acetate.

Another preferred class is the device wherein said solubilizing agent is an ionic surfactant having an aliphatic chain of 8 to 22 carbon atoms, especially where said ionic surfactant is cetyl pyridinium chloride, cetyl trimethylammonium bromide, cetyl trimethylammonium tosylate, or sodium lauryl sulfate, particularly sodium lauryl sulfate. A preferred subclass is the device wherein the sodium lauryl sulfate is present within the membrane at a concentration between 0.001% and 10%, preferably between 0.01% and 2.5%.

Another preferred class is the device wherein said hydrophilic non-toxic polymer is polyvinylpyrrolidone, starch, gelatin, methyl cellulose, sodium carboxymethylcellulose, hydroxypropyl methylcellulose, hydroxypropyl cellulose, or polyethylene glycol having a molecular weight between about 2000 and 20,000, especially polyethylene glycol 8000. A preferred subclass is the device wherein said polyethylene glycol 8000 is present within the membrane at a concentration between 0.01% and 40%.

Another preferred class of the invention is the device wherein said non-porous rate-controlling membrane comprises an aliphatic polyurethane, an aromatic polyurethane, a silicone rubber, a polyethylene-vinyl acetate copolymer, or a polystyrene-butadiene copolymer, especially an aliphatic polyurethane, and particularly Tecoflex ® polyurethane. A presently preferred subclass is the device wherein said rate-controlling membrane is between 0.05 and 1 mm in thickness and 1 and 10 cm² in surface area, preferably about 4 cm².

Another preferred class is the device which further comprises an amount of an antibiotic present within the solid formulation or on the outer surface of the rate-controlling membrane in an amount sufficient to prevent infection associated with implantation of said device.

A presently preferred embodiment is a reservoir device for the sustained administration of a biologically active compound, suitable for subcutaneous implantation, which device comprises: a pellet or plurality of pellets comprising 20–1,000 mg of progesterone, testosterone propionate, or trenbolone acetate; 2–100 mg of estradiol benzoate; 4–100 mg of polyethylene glycol 8000; and 0.2–10 mg of sodium lauryl sulfate; and 1–10 cm² of a non-porous, non-degradable rate-controlling membrane having a thickness between 0.05 and 1 mm, where said membrane is formed from Tecoflex ® polyurethane, and completely encapsulates said pellet or plurality of pellets.

Another presently preferred embodiment is the device wherein said pellet or plurality of pellets comprises about 200 mg of progesterone, about 20 mg of estradiol benzoate, about 44 mg of polyethylene glycol 8000, and about 5.2 mg of sodium lauryl sulfate.

Another presently preferred embodiment is the device wherein said pellet or plurality of pellets comprises about 200 mg of progesterone, about 20 mg of estradiol benzoate, about 44 mg of polyethylene glycol 8000, about 5.2 mg of sodium lauryl sulfate, and about 2–20 mg of oxytetracycline.

Another presently preferred embodiment is the device wherein said pellet or plurality of pellets comprises about 200 mg of testosterone propionate, about 20 mg of estradiol benzoate, about 44 mg of polyethylene glycol 8000, and about 5.2 mg of sodium lauryl sulfate.

Another presently preferred embodiment is the device wherein said pellet or plurality of pellets comprises about 200 mg of trenbolone acetate, about 20 mg of estradiol benzoate, about 44 mg of polyethylene glycol 8000, and about 5.2 mg of sodium lauryl sulfate. All of the preferred embodiments described above are capable of releasing an effective amount of the biologically active compounds over a period in excess of 230 days.

Another presently preferred embodiment is the device wherein said pellet or plurality of pellets comprises about 200 mg of progesterone, about 20 mg of estradiol benzoate, about 200 mg of trenbolone or trenbolone acetate, about 64 mg of polyethylene glycol 8000, and about 5.2 mg of sodium lauryl sulfate.

Another presently preferred embodiment is the device wherein said pellet or plurality of pellets comprises about 200 mg of testosterone propionate, about 20 mg of estradiol benzoate, about 200 mg of trenbolone or trenbolone acetate, about 64 mg of sodium lauryl sulfate.

Another aspect of the invention is a method for administering a biologically active compound to a subject in need thereof over an extended time period, which method comprises implanting subcutaneously a device of the invention. A preferred subgenus of the invention is the method which comprises subcutaneously administering a reservoir device comprising an effective amount of a weight gain promoting steroid, an amount of a solid, hydrophilic, non-toxic polymer sufficient to cause swelling by osmotic pressure after implantation, an effective amount of a solubilizing agent, and a sufficient amount of a non-porous, rate-controlling membrane which completely encapsulates said biologically active compound, wherein said rate-controlling membrane is permeable to said steroid, but is not permeable to said solubilizing agent or said solid hydrophilic polymer. A preferred class of the invention is the method wherein said device comprises a pellet or plurality of pellets comprising 20–1,000 mg of progesterone, testosterone propionate, or trenbolone acetate, 2–100 mg of estradiol benzoate, 4–100 mg of polyethylene glycol 8000, and 0.2–10 mg of sodium lauryl sulfate; and 1–10 cm² of a non-porous, non-degradable rate-controlling membrane having a thickness between 0.05 and 1 mm, where said membrane is formed from Tecoflex ® polyurethane, and completely encapsulates said pellet or plurality of pellets.

Another aspect of the invention is a method for administering a pharmaceutically acceptable steroid to a mammal to effect contraception, estrogen replacement therapy, or breast cancer treatment, which method comprises subcutaneously implanting a reservoir device comprising an effective amount of a pharmaceutically acceptable steroid, an amount of a solid hydrophilic polymer sufficient to cause swelling by osmotic pressure after implantation, an effective amount of a solubilizing agent, and a sufficient amount of a non-porous, rate-controlling membrane which completely encapsulates said biologically active compound, wherein said rate-controlling membrane is permeable to said steroid, but is not permeable to said solubilizing agent or said solid hydrophilic polymer.

DEFINITIONS

The term "biologically active compound" as used herein refers to a compound useful for effecting some beneficial change in the subject to which it is administered. For example, "biologically active compounds" within the scope of this definition include steroid hormones, prostaglandins, vitamins, antibiotics, antiinflammatory agents, chemotherapeutic agents, cardiovascular and antihypertensive agents, and the like. Preferred biologically active compounds within the invention are steroid hormones useful for promoting weight gain in livestock, especially estradiol benzoate, progesterone, testosterone propionate, and trenbolone acetate.

The term "pharmaceutically acceptable steroid" refers to a steroid hormone suitable for parenteral administration to a mammal, particularly a human. Suitable steroids include levonorgestrel, estradiol 17β, testosterone, testosterone propionate, ethynyl estradiol, and the like.

The term "effective amount" as applied to a biologically active compound refers to that amount which is sufficient to effect the desired change in the subject. For example, if the desired effect is human contraception, an effective amount is that amount sufficient to result in contraception, which amount may easily be determined by one of ordinary skill. Where the desired effect is increased weight gain in livestock, the "effective amount" is a "livestock weight gain-promoting" amount, and will vary depending on the species of animal subject.

The term "hydrophilic polymer" refers to a water imbibing polymer which is capable of drawing water into the implant after it is administered. This water intake serves to increase the diameter of the device after it is implanted, which decreases the probability that the device will fall out of the implant site, makes the device easier to implant, and increases the total membrane surface area, thus increasing the flux of biologically active compound. The hydrophilic polymers suitable for use in the invention are solid at room temperature. The hydrophilic polymer also prevents the formation of bubbles inside the capsule, and in some cases aids in solubilizing the biologically active compound. Suitable hydrophilic polymers include polyvinylpyrrolidone, starch, dried gelatin, methyl cellulose, sodium carboxymethylcellulose, hydroxypropyl methylcellulose, hydroxypropyl cellulose, or polyethylene glycol having a molecular weight between about 2000 and 20,000. High molecular weight polymers are preferred, due to their decreased ability to penetrate the rate-controlling membrane. The presently preferred hydrophilic polymer is polyethylene glycol (PEG) 8000.

The term "solubilizing agent" as used herein refers to a compound capable of increasing the solubility of the biologically active compound under aqueous conditions, e.g., by increasing the rate of dissolution of undissolved biologically active compound. Suitable solubilizing agents are essentially incapable of penetrating the rate-controlling membrane. The solubilizing agent is thus trapped within the membrane. This confinement serves to reduce the amount of solubilizing agent required, as a very small amount of a suitable solubilizing agent can solubilize enough biologically active compound to maintain the solution within the membrane at a high concentration. Additionally, this allows one to use solubilizing agents that would otherwise be too irritating or toxic for subcutaneous administration. Exemplary solubilizing agents are ionic surfactants having long (8-22 carbon atoms) aliphatic chains, for example, cetyl pyridinium chloride, cetyl trimethylammonium bromide, cetyl trimethylammonium tosylate, and sodium lauryl sulfate. The presently preferred solubilizing agent is sodium lauryl sulfate.

The term "effective amount" as applied to a solubilizing agent refers to the amount of solubilizing agent needed to maintain an appropriate concentration of biologically active compound in solution within the membrane-enclosed reservoir. The concentration of solubilizing agent needed to achieve an "effective amount" is a function of the biologically active compound and the membrane composition, thickness, and surface area, and may be determined by routine experimentation by one of ordinary skill in the art.

The term "rate-controlling membrane" refers to a polymer film, tube, or the like, which is permeable to the biologically active compound, but is impermeable to the solubilizing agent or the solid hydrophilic polymer. Rate-controlling membranes used herein are non-porous. The particular material used to prepare the rate-controlling membrane is selected based on its permeability to the biologically active compound, the availability of solubilizing agents incapable of diffusing through the material, and the suitability of the material for implantation under the subject's skin. Exemplary materials suitable for preparing rate-controlling membranes include, without limitation, aliphatic polyurethanes (for example Tecoflex ® polyurethane), aromatic polyurethanes, silicone rubbers (for example, polydimethylsiloxane, sold under the name Silastic ®), polyethylene-vinyl acetate copolymers, and polystyrene-butadiene copolymers. The presently preferred rate-controlling membrane is prepared by cutting a tube of Tecoflex ® polyurethane of the appropriate diameter to the desired length, filling the tube with a formulation containing the biologically active compound, and then sealing the ends of the tube using heat or adhesive. Another presently preferred method for preparing the implant is to form the rate-controlling membrane by injection molding with one end closed, filling the capsule, and sealing the open end. Alternatively, one may prepare rate-controlling membranes by wrapping the desired material around the biologically active compound and sealing the material, by dipping the biologically active compound into a vessel containing molten or dissolved polymer material, by spraying the material (or a solution thereof) to coat a solid formulation of biologically active compound, or by other methods known to those of ordinary skill in the art.

The term "Tecoflex ® polyurethane" refers to an aliphatic polyurethane polymer synthesized from methylene bis(cyclohexyl) diisocyanate, poly(tetramethylene ether glycol), and a 1,4-butanediol chain extender, having the following structure:

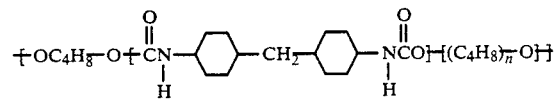

Tecoflex ® polyurethane is commercially available from Thermedics Corp., P.O. Box 1999, Woburn, Mass. 01888.

The term Silastic ® refers to a silicone rubber commonly used for implants, specifically polydimethylsiloxane. Silastic ® is commercially available from Dow Corning Co., Midland, Mich.

The term "sufficient amount" as applied to the rate-controlling membrane refers to the amount of surface area of membrane required to effect a flux of biologically active compound sufficient to achieve the desired purpose. The area necessary may be determined and adjusted directly by measuring the flux obtained with the particular biologically active compound and solubilizing agent selected. Preferably, the surface area is minimized where possible, to reduce the size of the implant. The minimum practical surface area will be that amount of membrane necessary to completely encapsulate the biologically active compound formulation. The maximum practical surface area depends on the species of the subject that will receive the implant. In one presently preferred embodiment of the invention, suitable for implantation in cattle, the implant device is a cylinder measuring approximately 32 mm by 3.9 mm (surface area = 3.9 cm$^2$).

The term "treatment" as used herein covers any treatment of a disease in an animal (including a human), and includes: (i) preventing the disease from occurring; (ii) inhibiting the disease, i.e., arresting its development; or (iii) relieving the disease, i.e., causing regression of the disease. Additionally, "treatment" includes modifications of normal biological activity such as contraception, synchronization of estrus, promotion or increase of weight gain, and the like.

PREPARATION

The manufacture of devices of the invention may be accomplished through a variety of methods. In the presently preferred method, a suitable formulation containing the biologically active compound, the solubilizing agent, and the hydrophilic polymer is prepared and compressed into cylindrical pellets or rods. An appropriate number of pellets or rods are inserted into a tube formed from the rate-controlling membrane, and the ends of the tube sealed by heat or adhesive. Preferably, the pellet diameter is approximately equal to the inside diameter of the rate-controlling membrane tube. This method is advantageous in that the cylindrical pellets are conveniently manipulated, and impart a degree of mechanical strength to the finished device. The complete device, comprising the stack of pellets sealed in the rate-controlling membrane, is rigid, which allows for convenient packaging and administration. Variations on this process are also possible, for example, one may seal one end of the rate-controlling membrane tube, or prepare the tube by injection molding with one end sealed, before inserting the pellet(s) or rod.

Alternatively, one may prepare a device of the invention by forming a pellet or rod containing the biologically active compound, the solubilizing agent, and the hydrophilic polymer, followed by wrapping the rod or pellet (or plurality of pellets) in a sheet of rate-controlling membrane. The membrane is then sealed using heat or adhesive. The pellets or rods are preferably cylindrical, but may be prepared in other forms having, for example, rectangular, hexagonal, octagonal, or elliptical shapes in cross-section.

Alternatively, one may prepare a device of the invention by dipping a solid pellet or rod containing the biologically active compound, the solubilizing agent, and the hydrophilic polymer into a solution or melt containing the rate-controlling membrane material. The dipping process may be repeated a number of times in order to obtain a rate-controlling membrane of the desired thickness.

Alternatively, one may prepare a device of the invention by spraying a solid pellet or rod containing the biologically active compound, the solubilizing agent, and the hydrophilic polymer with a solution or melt containing the rate-controlling membrane material.

If desired, one may substitute a powdered or granulated formulation for the compressed pellets or rods which are preferred. For example, one may prepare a device of the invention by combining the biologically active compound, the solubilizing agent, and the hydrophilic polymer in a powdered or granulated formulation, and load the formulation into tubes of rate-controlling membrane where one end is pre-sealed. After loading, the other end of the tube is sealed. Powder-filled and granulate-filled devices may be advantageous where greater flexibility is desired, for example, a device filled with a lightly-packed granulate may prove more suitable for administration to humans.

In any embodiment of the invention, one may additionally add an acceptable antibiotic to the outside of the completed device, or incorporate an acceptable antibiotic within the biologically active compound formulation. For example, a device may be dusted with a powdered antibiotic, or sprayed with a dilute solution of antibiotic and dried. Suitable antibiotics include, for example, oxytetracycline.HCl, gentimycin, and the like.

ADMINISTRATION AND FORMULATION

The sustained-release devices of the invention are designed for subcutaneous implantation, but may alternatively be administered to other body cavities, for example, vaginally, nasally, sublingually, and the like.

In one presently-preferred embodiment of the invention, a device is prepared for promoting growth in cattle. The device of the invention is implanted using a hollow needle implanting gun, for example of the type disclosed in U.S. Pat. No. 4,474,572, incorporated herein by reference. For administration to cattle, the implant is placed subcutaneously in the middle third of the subject's ear. Alternative sites of subcutaneous administration include the nape of the subject's neck and the axillary region. Other devices of the invention, when scaled to a suitable size, are suitable for similar implantation in sheep, swine, horses, and the like.

Another presently-preferred embodiment of the invention comprises a contraceptive or chemotherapeutic implant for humans. Such implants are most conveniently sited beneath the skin of the buttock or thigh.

The amount of biologically active compound administered via a device of the invention will vary depending on the identity of the compound; the size, age, weight, and species of the subject to be treated; the severity of the condition or the magnitude of the effect desired, and so forth. These parameters are easily determined and factored by one of ordinary skill in the art. For example, a representative device of the invention suitable for promoting growth in steers contains a combination of about 200 mg of progesterone and about 20 mg of estradiol benzoate as the biologically active compound. A representative device suitable for promoting growth in heifers contains a combination of about 200 mg of testosterone propionate and about 20 mg of estradiol benzoate as the biologically active compound.

Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Other suitable pharmaceutical carriers and their formulations are described in "Remington's Pharmaceutical Sciences" by E. W. Martin.

EXAMPLE 1

Preparation of Implants (A) A sustained release device of the invention, suitable for subcutaneous implantation in steers, was prepared as described below.

First, a solid pellet formulation was prepared:

| Progesterone | 25.0 mg |
| --- | --- |
| Estradiol Benzoate | 2.5 mg |
| Purified water | 1.0 mg |
| PEG 8000 (powdered) | 5.5 mg |
| Magnesium stearate | 0.1 mg |
| Methanol | 1.4 mg |
| Sodium lauryl sulfate | 0.7 mg |

The progesterone, estradiol benzoate, PEG 8000, and sodium lauryl sulfate were blended together, then granulated using the purified water and methanol. The granulate was dried and blended with the magnesium stearate, followed by tableting into pellets about 3.8 mm long by about 3.2 mm in diameter.

Eight of the resulting pellets were then inserted into a length of Tecoflex ® polyurethane tubing, having an inside diameter of about 3.4 mm and an outside diameter of about 3.9 mm. The ends of the tube were cut to length, leaving several millimeters at each end to seal the tube. The tube ends were then heat-sealed using a radio-frequency sealer.

(B) Similarly, proceeding as in part A above but substituting 25.0 mg of testosterone propionate for the progesterone, an implant suitable for administration to heifers was prepared.

(C) Similarly, proceeding as in part A above but substituting 25.0 mg of trenbolone acetate for the progesterone, an implant suitable for administration to heifers was prepared.

(D) Similarly, proceeding as in parts A-C above but adding 10 mg of oxytetracycline (Pfizer) to the solid formulation, implants suitable for administration to cattle were prepared.

(E) Similarly, implants suitable for administration to cattle were prepared proceeding as in parts A-C above, with 10 mg of finely powdered oxytetracycline (Pfizer) dusted on the outside of the implants.

(F) Similarly, proceeding as in parts A-E above, but substituting tubing of similar dimensions made from Silastic ®, polyethylene-vinyl acetate copolymer, and polystyrene-butadiene copolymer, implants suitable for administration to cattle were prepared.

(G) Another sustained release device of the invention, suitable for subcutaneous implantation in steers, was prepared as described below.

First, a solid pellet formulation was prepared:

| | |
|---|---|
| Trenbolone | 25.0 mg |
| Progesterone | 25.0 mg |
| Estradiol Benzoate | 2.5 mg |
| Purified water | 1.0 mg |
| PEG 8000 (powdered) | 7.5 mg |
| Magnesium stearate | 0.1 mg |
| Methanol | 1.4 mg |
| Sodium lauryl sulfate | 0.7 mg |

The trenbolone, progesterone, estradiol benzoate, PEG 8000, and sodium lauryl sulfate were blended together, then granulated using the purified water and methanol. The granulate was dried and blended with the magnesium stearate, followed by tableting into pellets about 6.6 mm long by about 4.0 mm in diameter.

Six of the resulting pellets were then inserted into a length of Tecoflex ® polyurethane tubing, having an inside diameter of about 4.2 mm and an outside diameter of about 4.7 mm. The ends of the tube were cut to length, leaving several millimeters at each end to seal the tube. The tube ends were then heat-sealed using a radio-frequency sealer.

(H) Similarly, proceeding as in part G above but substituting 25.0 mg of testosterone propionate for the progesterone, an implant suitable for administration to heifers was prepared.

(I) Similarly, proceeding as in parts G-H above but substituting trenbolone acetate for trenbolone, the corresponding implants are prepared.

EXAMPLE 2

In Vitro Zero Order Release

Implants are prepared according to the following scheme:

| Pellet | PG | EB | PEG | SLS | MGS | RCM |
|---|---|---|---|---|---|---|
| A | 25.0 | 2.5 | 5.5 | 0.7 | 0.1 | + |
| B | 25.0 | 2.5 | 0.0 | 0.7 | 0.1 | + |
| C | 25.0 | 2.5 | 5.5 | 0.0 | 0.8 | + |
| D | 25.0 | 2.5 | 0.0 | 0.0 | 0.8 | + |
| E | 25.0 | 2.5 | 5.5 | 0.7 | 0.1 | − |
| F | 25.0 | 2.5 | 0.0 | 0.7 | 0.1 | − |

-continued

| Pellet | PG | EB | PEG | SLS | MGS | RCM |
|---|---|---|---|---|---|---|
| G | 25.0 | 2.5 | 5.5 | 0.0 | 0.8 | − |
| H | 25.0 | 2.5 | 0.0 | 0.0 | 0.8 | − |

(PG = progesterone, EB = estradiol benzoate, PEG = powdered polyethylene glycol 8000, SLS = sodium lauryl sulfate, MGS = magnesium stearate, RCM = Tecoflex ® polyurethane capsule. All amounts are in mg.)

The pellets are prepared according to Example 1(A) and pellets A-D are loaded into Tecoflex ® polyurethane tubing to prepare implants A-D. Pellets E-H are not loaded, and are used without encapsulation. Each of the resulting preparations is then tested according to the following protocol:

Each preparation is placed in a 20 mL screw-top vial with 20 mL of sodium lauryl sulfate (0.1%) in phosphate buffer (pH 7.4). The vials are secured on their sides in a water bath shaker, and are shaken at about 20 one inch strokes per minute at 37° C. The solution in each vial is replaced daily, and is assayed for amount of progesterone and estradiol benzoate.

The results of this assay demonstrate that the preparation of the invention (A) is capable of releasing a biologically effective amount of progesterone and estradiol benzoate at a constant (zero order) rate for periods in excess of 200 days. In contrast, this assay demonstrates that those preparations lacking an essential element of the instant invention release progesterone and estradiol benzoate with first order or other kinetics, such that the release rate declines over the course of the experiment.

EXAMPLE 3

In Vivo Zero Order Release

Eight preparations (A-H) are prepared as in Example 2, and each is implanted subcutaneously in the middle third portion of the ear in steers weighing at least 300 pounds (with appropriate control animals). The animals are fed a finishing diet ad libitum, and the amounts of feed consumed recorded. On days 0, 28, 56, 84, 112, 140, 168, and 196 the animals are each weighed, and a sample of blood plasma taken. Average daily weight gain, feed efficiency, and plasma levels of steroids are measured and calculated. Any remaining implants are removed and assayed for remaining steroid.

The results of this experiment demonstrate that the devices of the invention are more effective than devices prepared without an essential element of the invention, and also that zero order release of the steroids is achieved.

EXAMPLE 4

Pharmaceutical Forms (A) An implant suitable for administration to humans for the treatment of breast cancer is prepared as follows:

| | |
|---|---|
| Testosterone | 9.0 mg |
| Purified water | 0.5 mg |
| PEG 8000 (powdered) | 2.0 mg |
| Magnesium stearate | 0.1 mg |
| Methanol | 0.7 mg |
| Sodium lauryl sulfate | 0.3 mg |

The testosterone, PEG 8000, and sodium lauryl sulfate were blended together, then granulated using the purified water and methanol. The granulate was dried and blended with the magnesium stearate, followed by tableting into pellets about 4.0 mm long by about 2.8 mm in diameter.

Four of the resulting pellets were then inserted into a length of Tecoflex ® polyurethane tubing, having an inside diameter of about 2.8 mm and an outside diameter of about 3.0 mm. The ends of the tube were cut to length, leaving several millimeters at each end to seal the tube. The tube ends were then heat-sealed using a radio-frequency sealer.

(B) An implant for effecting human contraception is prepared as follows:

| | |
|---|---|
| levonorgestrel | 15.0 mg |
| Purified water | 1.0 mg |
| PEG 8000 (powdered) | 2.8 mg |
| Magnesium stearate | 0.1 mg |
| Methanol | 0.7 mg |
| Sodium lauryl sulfate | 0.4 mg |

The ingredients are combined and tableted into pellets approximately 4.0 mm long by about 2.9 mm in diameter, then inserted into polyurethane tubing of the appropriate size and sealed, as in part A above.

(C) An implant suitable for administration to humans for estrogen replacement therapy is prepared as follows:

| | |
|---|---|
| estradiol 17β | 10.0 mg |
| Purified water | 0.5 mg |
| PEG 8000 (powdered) | 2.0 mg |
| Magnesium stearate | 0.1 mg |
| Methanol | 0.7 mg |
| Sodium lauryl sulfate | 0.3 mg |

The implant is prepared as in part A above.

What is claimed is:

1. A reservoir device for the sustained administration of a steroid hormone useful for promoting weight gain in livestock, suitable for subcutaneous implantation, which device comprises:
   a) a pellet or plurality of pellets, wherein each pellet comprises
      1) a steroid hormone in a livestock weight gain-promoting amount,
      2) a solid hydrophilic polymer in an amount sufficient to cause swelling of said device by osmotic pressure, and
      3) a solubilizing agent in an amount sufficient to maintain an effective concentration of said steroid hormone in solution within said device, wherein said solubilizing agent is an ionic surfactant having an aliphatic chain of 8 to 22 carbon atoms; and
   b) a sufficient amount of a non-porous, rate-controlling membrane which completely encapsulates said pellet or said plurality of pellets, wherein:
      1) said membrane is prepared from a material that is selected from the group consisting of an aliphatic polyurethane, an aromatic polyurethane, a silicone rubber, a polyethylene-vinyl acetate copolymer, and a polystyrene-butadiene copolymer; and
      2) said membrane is permeable to water and to said steroid hormone, but is impermeable to said solubilizing agent and said hydrophilic polymer.

2. The device of claim 1 wherein said steroid hormone comprises an estrogen derivative in combination with a progestogen, an androgen, or a combination thereof.

3. The device of claim 2 wherein said estrogen derivative is estradiol or an ester thereof.

4. The device of claim 3 wherein said steroid hormone comprises estradiol benzoate and progesterone.

5. The device of claim 3 wherein said steroid hormone comprises estradiol benzoate and testosterone or testosterone propionate.

6. The device of claim 3 wherein said steroid hormone comprises estradiol benzoate and trenbolone or trenbolone acetate.

7. The device of claim 3 wherein said steroid hormone comprises estradiol benzoate, progesterone, and trenbolone acetate.

8. The device of claim 3 wherein said steroid hormone comprises estradiol benzoate, testosterone propionate, and trenbolone acetate.

9. The device of claim 1 wherein said solubilizing agent is selected from the group consisting of cetyl pyridinium chloride, cetyl trimethylammonium bromide, cetyl trimethylammonium tosylate, and sodium lauryl sulfate.

10. The device of claim 9 wherein said solubilizing agent is sodium lauryl sulfate.

11. The device of claim 10 wherein the sodium lauryl sulfate is present at a concentration between 0.001% and 10%.

12. The device of claim 11 wherein the sodium lauryl sulfate concentration is about 0.01% to 2.5%.

13. The device of claim 1 wherein said hydrophilic polymer is selected from the group consisting of polyvinylpyrrolidone, starch, gelatin, methyl cellulose, sodium carboxymethylcellulose, hydroxypropyl methylcellulose, hydroxypropyl cellulose, and polyethylene glycol having a molecular weight between about 2000 and 20,000.

14. The device of claim 13 wherein said hydrophilic polymer is a polyethylene glycol having a molecular weight of about 8000.

15. The device of claim 14 wherein said polyethylene glycol is present at a concentration of about 0.01% to 40%.

16. The device of claim 1 wherein said membrane is an aliphatic polyurethane.

17. The device of claim 16 wherein said aliphatic polyurethane is synthesized from methylene bis(cyclohexyl) diisocyanate, poly(tetramethylene ether glycol), and a 1,4-butanediol chain extender and has the following structure:

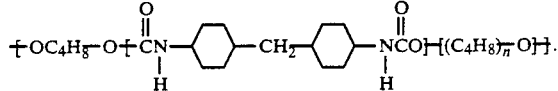

18. The device of claim 17 wherein said membrane is between about 0.05 and about 1 mm in thickness.

19. The device of claim 18 wherein said membrane has a surface area between about 1 and about 10 cm².

20. The device of claim 1 wherein said pellet or plurality of pellets comprises:
   about 20–1,000 mg of progesterone, testosterone propionate, trenbolone, or trenbolone acetate;
   about 2–100 mg of estradiol benzoate;
   about 4–400 mg of a polyethylene glycol having a molecular weight of about 8000; and about 0.2–10 mg of sodium lauryl sulfate; and
wherein said membrane has a surface area between about 1 and 10 cm², a thickness between about 0.05 and about 1 mm, and is prepared from an aliphatic polyurethane which is synthesized from methylene bis(cyclohexyl) diisocyanate, poly(tetramethylene ether glycol), and a 1,4-butanediol chain extender and has the following structure:

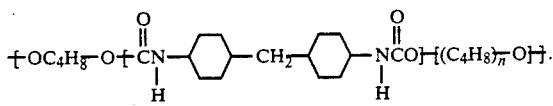

21. The device of claim 20 wherein said pellet or plurality of pellets comprises:
   about 200 mg of progesterone;
   about 20 mg of estradiol benzoate;
   about 44 mg of a polyethylene glycol having a molecular weight of about 8000; and
   about 5.2 mg of sodium lauryl sulfate.

22. The device of claim 20 wherein said pellet or plurality of pellets comprises:
   about 200 mg of testosterone propionate;
   about 20 mg of estradiol benzoate;
   about 44 mg of a polyethylene glycol having a molecular weight of about 8000; and
   about 5.2 mg of sodium lauryl sulfate.

23. The device of claim 20 wherein said pellet or plurality of pellets comprises:
   about 200 mg of trenbolone acetate;
   about 20 mg of estradiol benzoate;
   about 44 mg of a polyethylene glycol having a molecular weight of about 8000; and
   about 5.2 mg of sodium lauryl sulfate.

24. The device of claim 20 wherein said pellet or plurality of pellets comprises:
   about 200 mg of trenbolone or trenbolone acetate;
   about 200 mg of progesterone;
   about 20 mg of estradiol benzoate;
   about 64 mg of a polyethylene glycol having a molecular weight of about 8000; and
   about 5.2 mg of sodium lauryl sulfate.

25. The device of claim 20 wherein said pellet or plurality of pellets comprises:
   about 200 mg of trenbolone or trenbolone acetate;
   about 200 mg of testosterone propionate;
   about 20 mg of estradiol benzoate;
   about 64 mg of a polyethylene glycol having a molecular weight of about 8000; and
   about 5.2 mg of sodium lauryl sulfate.

26. The device of claim 1 which further comprises an antibiotic present in an amount sufficient to prevent infection associated with implantation of said device, wherein said antibiotic is selected from the group consisting of oxytetracycline, oxytetracycline.HCL and gentimycin.

27. The device of claim 26 wherein said antibiotic is present on the outer surface of said membrane.

28. A method for promoting weight gain and increasing feed efficiency in livestock, which method comprises:
subcutaneously administering a reservoir device which device comprises:
   a) a pellet or plurality of pellets, wherein each pellet comprises:
      1) a steroid hormone in a livestock weight gain-promoting amount,
      2) a solid hydrophilic polymer in an amount sufficient to cause swelling of said device by osmotic pressure, and
      3) a solubilizing agent in an amount sufficient to maintain an effective concentration of said steroid hormone in solution within said device, wherein said solubilizing agent is an ionic surfactant having an aliphatic chain of 8 to 22 carbon atoms; and
   b) a sufficient amount of a non-porous, rate-controlling membrane which completely encapsulates said pellet or said plurality of pellets, wherein:
      1) said membrane is prepared from a material that is selected from the group consisting of an aliphatic polyurethane, an aromatic polyurethane, a silicone rubber, a polyethylene-vinyl acetate copolymer, and a polystyrene-butadiene copolymer; and
      2) said membrane is permeable to water and to said steroid hormone, but is impermeable to said solubilizing agent and said hydrophilic polymer.

29. The method of claim 28 wherein said pellet or plurality of pellets comprises:
   20–1,000 mg of progesterone, testosterone, testosterone propionate, trenbolone, or trenbolone acetate;
   2–100 mg of estradiol benzoate;
   4–400 mg of a polyethylene glycol having a molecular weight of about 8000; and
   0.2–10 mg of sodium lauryl sulfate; and
wherein said membrane has a surface area between about 1 and 10 cm², a thickness between about 0.05 and about 1 mm, and is prepared from an aliphatic polyurethane which is synthesized from methylene bis(cyclohexyl) diisocyanate, poly(tetramethylene ether glycol), and a 1,4-butanediol chain extender and has the following structure:

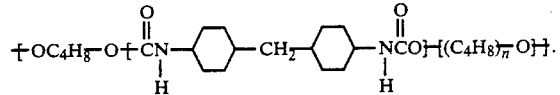

* * * * *